US00PP09953P

United States Patent [19]

Mak

[11] Patent Number: Plant 9,953

[45] Date of Patent: Jul. 8, 1997

[54] LILIUM PLANT NAMED 'RUBY FLASH'

[76] Inventor: Johan A. Mak, 5595 Halls Ferry Rd., Independence, Oreg. 97351

[21] Appl. No.: 618,476

[22] Filed: Mar. 18, 1996

[51] Int. Cl.[6] ..... A01H 5/00

[52] U.S. Cl. ..... Plt./87.4

[58] Field of Search ..... Plt./87.4

*Primary Examiner*—Howard J. Locker

[57] ABSTRACT

A new variety of hybrid lily plant bearing medium size out-facing flowers of excellent form and long persistence, both on the plant and as pot flowers. The flowers of the new plant are particularly characterized by their pink coloration shading into a reddish band at the midrib, their lightly ruffled margins, their almost flat shape and heavy substance, their out-facing orientation, and the showing of color on almost all of the upper buds. This combination is completely new in the Oriental Hybrid divisions of the lilies suited to pot forcing and to mass commercial cultivation. The variety is highly resistant to fusarium disease and shows tolerance of virus. The bulbs may be precooled and forced for cut-flower production. The clone is vigorous and is a good grower and propagator.

1 Drawing Sheet

BACKGROUND OF THE INVENTION

My new variety of lily plant originated as a seedling which first flowered in 't Zand, Netherlands, in 1988. The breeding efforts had as their objective the production of out-facing flowered or semi-upright Oriental hybrids in bicolor combinations of soft pink and red, with pigmented papillae, suited to pot forcing into flower out of season, heretofore unknown in the lily breeding art. I achieved the desired objective by intercrossing selected short out-facing and semi-upright pink and red Oriental seedlings suited to forcing for year-round use as pot cultivars and carrying the recessive gene for a reddish center. The flowers of my new lily are characterized by an out-facing orientation, medium size and broad-tepalled "bowl-shaped" form, unusually thick substance, ruffled tepal margins, and a distinctive soft pink coloration shading into a reddish colored center, unique among Oriental hybrid lilies for pot forcing purposes. The pedicels of the upper flowers are ascending. It possesses unusually strong, short stems. In addition, the plant possesses to a high degree desirable characteristics of hybrid vigor. The plant is a good grower and propagator, as observed at 't Zand, Netherlands, and at Independence, Oreg. My new variety of lily plant has been asexually reproduced by me and under my direction at 't Zand, Netherlands, and at Independence, Oreg. Successive generations produced by natural propagation from bulblets, by bulb scale propagation, and by tissue culturing from bulb scale explants have demonstrated that the novel and distinctive characteristics of my new variety are fixed and hold true under asexual propagation from generation to generation.

DESCRIPTION OF THE DRAWING

My new variety of lily plant is illustrated in the accompanying photographic drawing, which shows the open bloom in full color and illustrates the flower form, the tepal arrangement, the ascending pedicels connecting the flower to the stem, and in particular the novel and distinctive flower form with lightly ruffled tepal margins, its out-facing orientation, and its soft pink coloration shading into a reddish banded midrib as well as the showing of color on most of the upper buds at the time the lowermost flowers first open.

DESCRIPTION OF THE VARIETY

The following is a detailed description of my new pot variety of Oriental hybrid lily, with nomenclature according to the International lily register (Royal Horticultural Society of London, Second Edition, 1969, and with color designations according to the Color Chart of The Royal Horticultural Society, published by the Society in 1969).

THE PLANT

Origin: Seedling.

Seed parent: Selected unnamed Oriental hybrid seedling.

Pollen parent: Selected unnamed Oriental hybrid seedling.

Commercial classification: Hybrid Lilium clone.

Horticultural classification: Division VII-B, bowl-shaped Oriental hybrid lily, according to the Horticultural Classification of Lilies, Royal Horticultural Society of London.

Form: Single stem, erect and stately.

Height: 35 to 45 cm. from bulbs 14 to 18 cm. in circumference, provided their light levels are adequate; low light levels may cause "stretching".

Growth: Vigorous and upright.

Foliage quantity: Abundant.

Size of leaf: Unusually broad, 4 to 7 cm. wide×8 to 11 cm. long.

Shape of leaf: Lanceolate (pointed).

Texture: Leathery and glossy.

Color: Dark green, lighter on lower side.

Bulb size: Any size, ranging to 25 cm. circumference commercially.

Bulb color: White, with flushes of pink or yellow after exposure to light.

THE BUD

Form: Obtuse, ovoid, and long.

Size: 8 to 12 cm. long and 10 to 13 cm. in circumference just prior to opening.

Opening: Bud opens slowly, in response to morning light; this takes about one hour.

Color: Ivory white to soft pink (R.H.S. CC red 49 D to red 56 D), with pale green midribs.

Peduncle: Averages 4 to 6 cm. but it may elongate if light levels are too low or if bulbs have been improperly stored prior to forcing. Color is medium green with very light plum overlay.

THE FLOWER

Blooming habit: Annually in mid season; flowers once and profusely.

Size: Flowers are large-sized, averaging 13 to 15 cm. in diameter, reflecting at the tips on the second day to 14 to 16 cm. in diameter. The tepals are broad; outer tepals are 2.5 to 3.25 cm. wide, and the inner tepals are 4.5 to 5 cm. wide.

Borne: In a single raceme inflorescence producing 3 to 5 flowers from a bulb 14 to 16 cm. in circumference.

Shape: Form a broad bowl shape by the second day after opening, with the "bowl" 9 cm. deep.

Tepalage: Typical of genus Lilium, with 6 imbricated tepals.

Tepal color: R.H.S. CC red purple 65 B to red-purple 62 D, depending upon growing, temperatures and light levels, shading into a reddish center R.H.S. CC Red 44 C to 44 D, extending 4 to 8 cm. from the green nectaries. The pink color is slightly affected by temperature and light levels; it decreases with high temperatures and low light levels.

Tepal spotting: The basal half of each tepal is spotted with magenta rose papillae of moderate size.

Tepal longevity: Tepals stay on stems about three weeks.

Pedicel length: Average 8 to 12 cm. long.

Pedicel color: Medium green with very light plum overlay.

Pedicel form: Sturdy and ascending, up to 60 degrees from the horizontal in the upper flowers.

Color changes: Flowers become slightly lighter and a more lavender-toned pink as the flowers age. Low light levels and extreme heat may cause the pink pigmentation to decrease.

Appearance: Flower is shiny.

Disease resistance: The flower and plant are resistant to disease; in particular, they are resistant to Fusarium bulb rot and Botrytis blight.

Fragrance: Light sweet fragrance.

Lasting quality: The flower is long lasting, both on the plant and as a cut-flower.

THE REPRODUCTIVE ORGANS

Stamens: Arrangement typical of genus Lilium. Six stamens with soft green to palest pink filaments 6 to 8 cm. long.

Pollen and anthers (dehisced): R.H.S. CC Orange red 33 A to 34 B.

Pistil: One in number, 7 to 9 cm. long.

Stigma: R.H.S. CC Black 202D, large in size.

Characteristics of ovary: Characteristics of genus Lilium.

THE FRUIT

Fertility: The fruit bears fertile seed.

Shape: Ovoid.

Color at maturity: Soft brown, sometimes overlaid with soft plum.

My new variety of Oriental hybrid lily most nearly resembles "Rio", but it has thicker, more bowl-shaped flowers with more ruffled tepal margins. Its flowers have a more conspicuous red midrib, as well as a greater number of more deeply colored papillae. Its pedicels are more sharply ascending.

I claim:

1. A new and distinctive variety of Oriental pot hybrid lily plant substantially as herein shown and described, characterized by its high resistance to disease; its tolerance of virus; its vigorous growth and rapid natural propagation; the excellence of its flower form, size, and substance; its versatility both as a garden plant and as a pot-flower producer from pre-cooled bulbs forced under glass out of season; and in particular by its unique out-facing flowers with strong pedicels, its lightly ruffled tepal margins, and its soft pink coloration shading into a reddish midrib, accented with noticeable magenta rose papillae on the basal half of each tepal and its pink coloration of the upper buds at the time the lowermost buds first open, a combination unique among Oriental hybrid lilies suited to pot forcing and to mass commercial cultivation.

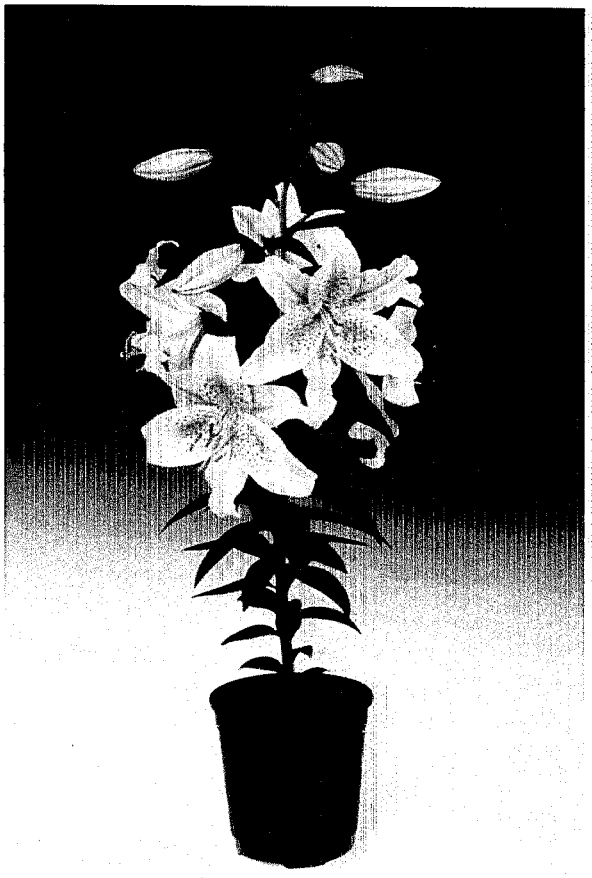

* * * * *